(12) United States Patent
Johs et al.

(10) Patent No.: US 6,549,282 B1
(45) Date of Patent: Apr. 15, 2003

(54) METHODS FOR UNCORRELATED EVALUATION OF PARAMETERS IN PARAMETERIZED MATHEMATICAL MODEL EQUATIONS FOR LENS RETARDANCE, IN ELLIPSOMETRY AND POLARIMETRY SYSTEMS

(75) Inventors: Blaine D. Johs, Lincoln, NE (US); Craig M. Herzinger, Lincoln, NE (US); Ping He, Lincoln, NE (US); Martin M. Ciphardt, Lincoln, NE (US)

(73) Assignee: J. A. Woollam Co. Inc., Lincoln, NE (US)

( * ) Notice: Subject to any disclaimer, the term of this patent is extended or adjusted under 35 U.S.C. 154(b) by 0 days.

(21) Appl. No.: 09/419,794

(22) Filed: Oct. 18, 1999

Related U.S. Application Data

(63) Continuation-in-part of application No. 09/162,217, filed on Sep. 29, 1998, now Pat. No. 6,034,777, and a continuation-in-part of application No. 09/033,694, filed on Mar. 3, 1998, now Pat. No. 5,963,327, and a continuation-in-part of application No. 09/144,764, filed on Aug. 31, 1998, now Pat. No. 5,969,818.

(51) Int. Cl.$^7$ .................................................. G01B 11/06
(52) U.S. Cl. ......................................................... 356/369
(58) Field of Search ................................. 356/365, 366, 356/369; 250/225

(56) References Cited

U.S. PATENT DOCUMENTS

| | | | | |
|---|---|---|---|---|
| 4,668,086 A | * | 5/1987 | Redner | 356/327 |
| 4,671,657 A | | 6/1987 | Calvani et al. | 356/349 |
| 5,166,752 A | | 11/1992 | Spanier et al. | 356/369 |
| 5,349,471 A | * | 9/1994 | Morris et al. | 359/565 |
| 5,757,494 A | * | 5/1998 | Green et al. | 250/225 |
| 5,872,630 A | * | 2/1999 | Johs et al. | 250/225 |
| 5,877,859 A | * | 3/1999 | Aspnes et al. | 250/225 |
| 5,963,327 A | | 10/1999 | He et al. | 356/369 |
| 5,978,087 A | * | 11/1999 | Patterson et al. | 356/33 |
| 6,034,777 A | * | 3/2000 | Johs et al. | 356/369 |

FOREIGN PATENT DOCUMENTS

JP 229720 2/1994

OTHER PUBLICATIONS

WO 91/14157 Published PCT Application.
WO 92/12404 Published PCT Application.
WO 96/18205 Published PCT Application.
WO 99/02950 Published PCT Application.

* cited by examiner

Primary Examiner—Zandra Smith
(74) Attorney, Agent, or Firm—James D. Welch

(57) ABSTRACT

Disclosed are ellipsometer and polarimeter systems which have multi-element input and output lenses that demonstrate essentially the same focal length at each wavelength in a spectroscopic range of wavelengths.

2 Claims, 4 Drawing Sheets

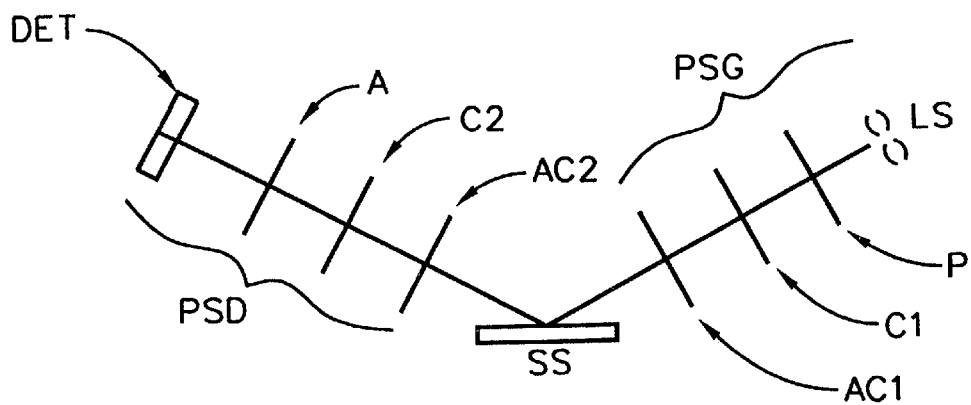
FIG. 1a₁
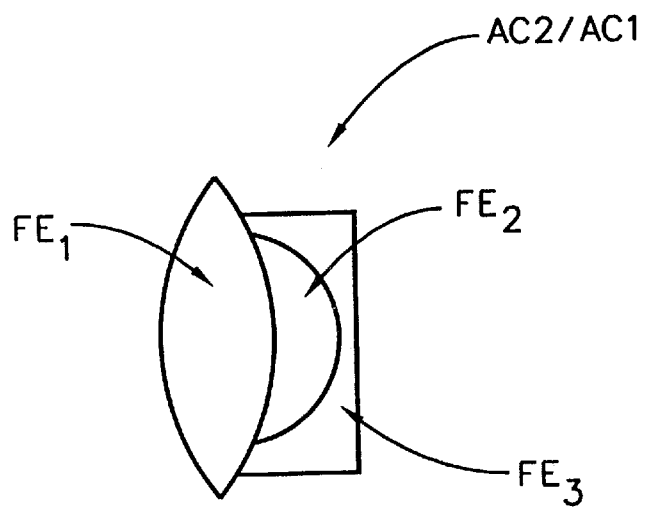
FIG. 1a₂

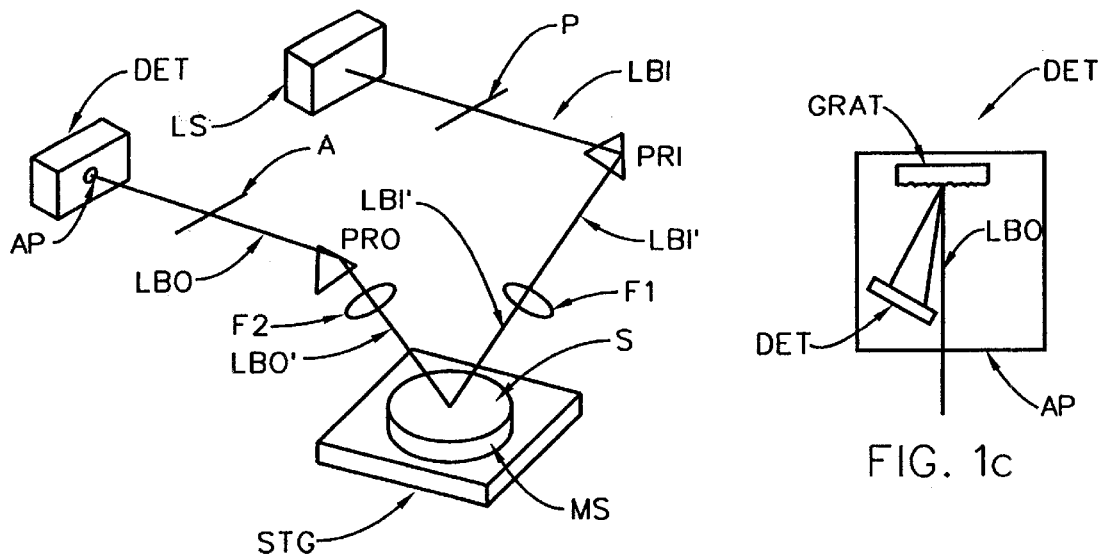
FIG. 1a₃
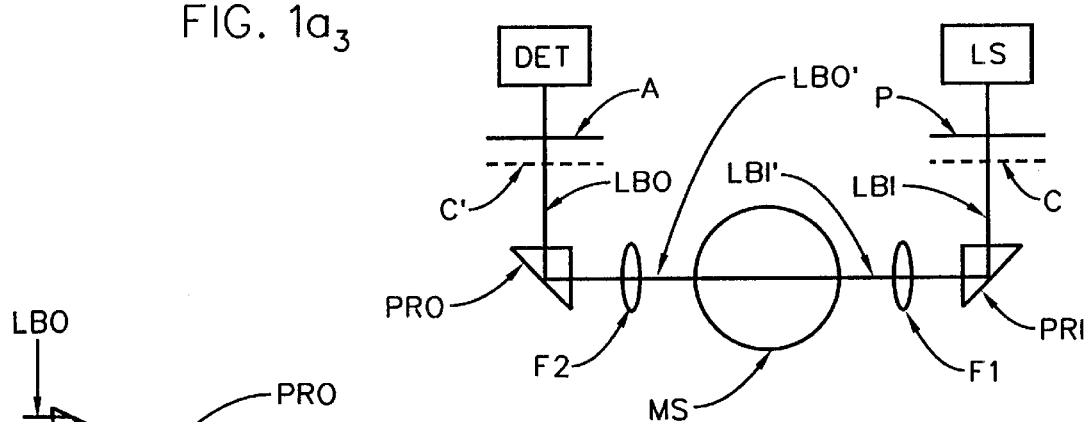
FIG. 1c
FIG. 2
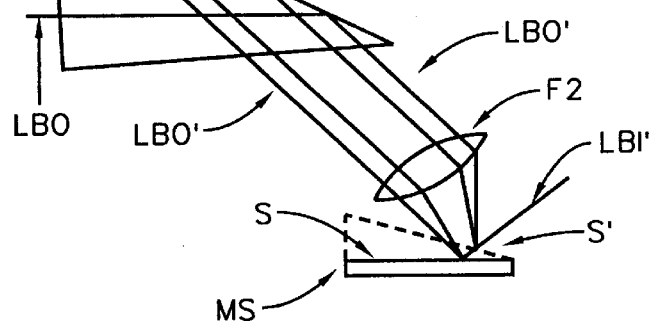
FIG. 1b

METHODS FOR UNCORRELATED EVALUATION OF PARAMETERS IN PARAMETERIZED MATHEMATICAL MODEL EQUATIONS FOR LENS RETARDANCE, IN ELLIPSOMETRY AND POLARIMETRY SYSTEMS

This Application is a Continuation-In-Part of Allowed application Ser. No. 09/162,217 filed Sep. 29, 1998 now U.S. Pat. No. 6,034,777, and of Allowed application Ser. No. 09/033,694 filed Mar. 3, 1998 now U.S. Pat. No. 5,963,327, and of Allowed application Ser. No. 09/144,764, filed Aug. 31, 1998 now U.S. Pat. No. 5,969,818, which depends from the 694 Application.

TECHNICAL FIELD

The present invention relates to ellipsometry and polarimetry, and more particularly is a system for focusing an electromagnetic beam as a small spot over a large range of wavelengths including into the deep UV, and further is a method for evaluating parameters in parameterized equations for calculating retardance entered to orthogonal components in a beam of electromagnetic radiation, by multiple element input and output lenses, through which said beam of electromagnetic radiation is caused to pass.

BACKGROUND

The practice of ellipsometry is well established as a non-destructive approach to determining characteristics of sample systems, which can be practiced in real time. The topic is well described in a number of publication, one such publication being a review paper by Collins, titled "Automatic Rotating Element Ellipsometers: Calibration, Operation and Real-Time Applications", Rev. Sci. Instrum, 61(8) (1990).

In general, the practice of ellipsometry typically involves causing a spectroscopic beam of electromagnetic radiation, in a known state of polarization, to interact with a sample system at some angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry determines said changes in polarization state by proposing a mathematical model of the ellipsometer system and the sample system investigated by use thereof. Experimental data is then obtained by application of the ellipsometer system, and a square error reducing mathematical regression, (typically), is then applied to the end that parameters in the mathematical model which characterize the sample system are evaluated so that the obtained experimental data, and values calculated by use of the mathematical model are essentially identical.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system;

$$PSI = |r_p/r_s|;$$

and $$DELTA = \angle r_p - \angle r_s)).$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Detector System.

Each of said components b.–i. must be accurately represented by a mathematical model of the ellipsometer system along with a vector which represents a beam of electromagnetic radiation provided from said source of a beam electromagnetic radiation, Identified in a. above)

Various ellipsometer configurations provide that a Polarizer, Analyzer and/or Compensator(s) can be rotated during data acquisition, and are describe variously as Rotating Polarizer (RAE), Rotating Analyzer (RAE) and Rotating Compensator (RCE) Ellipsometer Systems.

Where an ellipsometer system is applied to investigate a small region of a sample system present, it must be appreciated that the beam of electromagnetic radiation can be entered thereto through an converging input lens, and exit via a diverging output lens. In effect this adds said converging input and diverging output lenses as elements in the ellipsometer system as "additional elements", (eg. identified in d. and f. above), which additional elements must be accounted for in the mathematical model. If this is not done, sample system representing parameters determined by application of the ellipsometer system will have the effects of said converging input and diverging output lenses at least partially correlated thereinto, much as if the converging input and diverging output lenses were integrally a part of the sample system.

It is further noted that where two sequentially adjacent elements in an ellipsometer system are held in a static position with respect to one another while experimental ellipsometric data is acquired, said two sequentially adjacent elements generally appear to be a single element. Hence, a beam directing element adjacent to a lens can appear indistinguishable from said lens as regards the overall effect of said combination of elements. In that light it is to be understood that converging input and diverging output lenses are normally structurally fixedly positioned and are not rotatable with respect to a sample system present in use, thus preventing breaking correlation between parameters in equations for sequentially adjacent converging input and diverging output lenses and an investigated sample system by an element rotation technique. While correlation of parameters in mathematical equations which describe the effects of groupings of elements, (such as a compensator and an optional element(s)), can be tollerable, correlation between parameters in the mathematical model of an investigated sample system and other elements in the ellipsometer system must be broken to allow obtaining accurate sample system representing PSI and DELTA values, emphasis added. That is to say that correlation between parameters in a equations in a mathematical model which describe the effects of a stationary compensator and a sequentially next lens element, (eg. correllation between effects of elements c. and d. or between f. and g. identified above), in a beam of electromagnetic radiation might be tolerated to the extent that said correlation does not influence determination of sample system describing PSI and DElTA values, but the correlation between parameters in equations which describe the effects of ellipsometer system components (eg. a., b., c., d., f., g., h. and i.), and equations which describe the effects of a present sample system (eg. element e. above), absolutely must be broken to allow the ellipsometer system to provide accurate PSI and DELTA values for said sample system. In-situ application of ellipsometry to investigation of a sample system present can then present a challenge to users of ellipsometer systems in the form of providing a mathematical model for each of a converging input and diverging output lens, and providing a method by which the effects of said converging input and diverging output lenses can be separated from the effects of an investigated sample system.

Thus is identified an example of a specific problem, solution of which is the topic of the present invention.

One typical approach to overcomming the identified problem, where space considerations are not critical, and where ellipsometer system configuration can be easily modified, is to obtain multiple data sets with an ellipsometer system configured differently during at least two different data set acquisitions. For instance, a data set can be obtained with a sample system present and in which a beam of electromagnetic radiation is caused to interact with said sample system, and another data set can be obtained with the ellipsometer system configured in a straight-through configuration, where a beam of electromagnetic radiation is caused to pass straight through an ellipsometer system without interacting with a sample system. Simultaneous mathematical regression utilizing both data sets can allow evaluation of sample system characterizing PSI and DELTA values over a range of wavelengths, uncorrelated with present bi-refringent retardation effects of said converging input and diverging output lenses. The problem with this approach is that where ellipsometer systems are fit to vacuum chambers for instance, ellipsometer reconfiguration so as to allow acquisition of such multiple data sets can be extremely difficult, if not impossible to carry out.

Another rather obvious solution to the identified problem is to provide converging input and diverging output lenses which are absolutely transparent at all electromagnetic beam wavelengths utilized. That is, provide converging input and diverging output lenses which do not attenuate the magnitude of $r_p$ or $r_s$ orthogonal components, (or at least do not change their ratio, $r_p/r_s$), and which also do not enter phase shift between $r_p$ or $r_s$ orthogonal components when said beam of electromagnetic radiation is caused to pass therethrough. While control of the the effect of a lens on a ratio, $(r_p/r_s)$, of electromagnetic beam orthogonal components can often rather successfully be accomplished by causing a beam of electromagnetic radiation to approach a surface of a lens along a normal to a surface thereof, this is not the case regarding phase shift entered between $r_p$ and $r_s$ orthogonal components of a said beam of electromagnetic radiation caused to pass therethrough. That is, converging input and diverging output lenses can demonstrate "bi-refringence", in that the $r_p$ orthogonal component is "retarded" by a different amount than is the $r_s$ orthogonal component when said beam of electromagnetic radiation is caused to pass therethrough.

To complicate matters, this "bi-refringent" effect also varies with wavelength and with stresses which can develop in a lens during use because of temperature and physical changes etc.

As described in Co-pending application Ser. No. 09/162, 217, (which is incorporated herein by reference), controlling stress related change is presently achieved with varying degrees of success, where for instance, windows in a vacuum chamber are subject. Windows provided by BOMCO Inc. are produced with the goal of eliminating bi-refringence, and are mounted in vacuum chambers using "O" ring seals which help to minimize uneven application of stresses and developed strains thereacross. While some success is achieved via this approach, the BOMCO windows are not "perfect" and do demonstrate some remaining bi-refringence properties, which can an vary in unpredictable ways over a period of usage. In addition, BOMCO windows are expensive, costing on the order of $1000.00 each), and are large in size thereby making adaptation thereof to use in a vacuum chamber difficult at times, particularly in retro-fit scenarios. And, there have been cases where BOMCO windows have broken in use. This is highly undesirable as vacuum chambers are often times caused to contain highly toxic and hazardous materials during, for instance, etching and/or deposition steps required in the fabrication of semiconductor devices. Where vacuum chamber windows are the subject, an alternative to use of the BOMCO windows is to simply use standard vacuum chamber windows, which, while significantly less expensive, demonstrate order of magnitude larger bi-refringence effects. (Note, BOMCO windows provide bi-refringent effects on the order of approximately six-tenths (0.6) to two-tenths (0.2) degrees over a range of wavelengths of from four-hundred (400) to seven-hundred-fifty (750) nanometers, whereas standard vacuum windows demonstrate birefringent effects on the order of six (6.0) to three (3.0) degrees over the same range of wavelengths). (Note, bi-refringent retardation typically follows an approximate inverse wavelength, (eg. 1/wavelength), relationship). However, where standard vacuum chamber windows are utilized, compensation of their effects is required. Similar concerns apply where converging input and diverging output lenses, and associated ellipsometrically indistinguishable ellipsometer system components are on point.

A need is thus identified for a method of practicing ellipsometry which enables the breaking of correlation between parameters in equations which describe retardance entered to orthogonal components of a beam of electromagnetic radiation caused to interact with a sample system, and parameters in equations which describe bi-refringent effects on said orthogonal components in said beam of electromagnetic radiation caused by input and output windows of a vacuum chamber, and/or by converging input and diverging output lenses etc.

Various researchers have previously noted the identified problem, where vacuum chamber windows are the topic, and proposed various first order mathematical model equation correction techniques as solution, which approaches have met with various degrees of success where vacuum chamber input and output windows demonstrate on the order of a maximum of two (2) degrees of bi-refringence. This, however, leaves the problem unsolved where bi-refringence approaches six (6.0) degrees, as commonly occures in standard vacuum chamber windows, and can also occur in lens systems, particlarly at wavelengths of four-hundred (400) nanometers and below.

Patents of which the Inventor is aware include U.S. Pat. No. 5,757,494 to Green et al., in which is taught a method for extending the range of Rotating Analyzer/Polarizer ellipsometer systems to allow measurement of DELTAS near zero (0.0) and one-hundred-eighty (180) degrees. Said Patent describes the presence of a window-like variable bi-refringent components which is added to a Rotating Analyzer/Polarizer ellipsometer system, and the application thereof during data acquisition, to enable the identified capability.

A Patent to Thompson et al. U.S. Pat. No. 5,706,212 teaches a mathematical regression based double fourier series ellipsometer calibration procedure for application, primarily, in calibrating ellipsometers system utilized in infrared wavelength range. Bi-refringent window-like compensators are described as present in the system thereof, and discussion of correlation of retardations entered by sequentially adjacent elements which do not rotate with respect to.one another during data acquisition is described therein.

A Patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertian to Rotating Analyzer ellipsometer systems.

Patents identified in a Search specifically focused on the use of lenses, preferrably achromatic, in ellipsometry and realted systems are:

U.S. Pat. Nos. 5,877,859 and 5,798,837 to Aspnes et al.;

U.S. Pat. No. 5,333,052 to Finarov;

U.S. Pat. No. 5,608,526 to Piwonka-Corle et al.;

U.S. Pat. No. 5,793,480 to Lacy et al.;

U.S. Pat. Nos. 4,636,075 and 4,893,932 to Knollenberg; and

U.S. Pat. No. 4,668,860 to Anthon.

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Nijs & Silfhout, titled "Systematic and Ramdom Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (September 1994) describes first order corrections for imperfections in windows and compensators in Rotating Compensator ellipsometers.

Principal component analysis and neural network approaches to the problem are discussed in a paper by Pickering et al, titled "Instrumental and Computational Advances for Real-time Processes Control Using Spectroscopic Ellipsometry", Int. Conf. on Netrology and Charcterization for VSLI Tech., NIST, (March 1998).

Other papers of interest in the area by Azzam & Bashara include one titled "Unified Analysis of Ellipsometry Erors Due to Imperfect Components Cell-Window Birifringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment Of Optical Systems", J.O.S.A., Voil. 31, (July 1941), is also identified as it describes the characterizing of multiple lens elements as a single lens.

Finally, A paper which is co-authored by the inventor herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol.406, (1996) is also disclosed.

In view of relevant prior art, and the inability of first order corrections to break correlation, there remains need for a second order mathematical model equation correction technique which enables breaking correlation between sample system characterization DELTA and in-plane retardance entered to a beam of electromagnetic radiation entered by converging input and diverging output lenses through which said beam of electromagnetic radiation is caused to pass. This is particularly true where lens bi-refringent retardance exceeds a few degrees, as and can be the case.

DISCLOSURE OF THE INVENTION

The present invention is primarily a method of accurately evaluating parameters in parameterized equations in a mathematical model of a system of spatially separated converging input and diverging output lenses, as applied in an ellipsometry or polarimetry setting. Said parameterized equations enable, when parameters therein are properly evaluated, independent calculation of retardation entered by each of said converging input lens and said diverging output lens between orthogonal components of a beam of electromagnetic radiation caused to pass through said converging input and diverging output lenses. (It is to be understood that at least one of said converging input and diverging output lenses is typically considered to be at least somewhat birefringent). In a basic sense, said method comprises, in a functional order, the steps of:

a. providing spatially separated converging input and diverging output lenses, at least one of said converging input diverging output lenses demonstrating birefringence when a beam of electromagnetic radiation is caused to pass therethrough, there being a means for supporting a sample system positioned between said converging input and diverging output lenses;

b. positioning an ellipsometer system source of electromagnetic radiation and an ellipsometer system detector system such that in use a beam of electromagnetic radiation provided by said source of electromagnetic radiation is caused to pass through said converging input lens, interact with said sample system in a plane of incidence thereto, and exit through said diverging output lens and enter said detector system;

c. providing a sample system to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said converging input and diverging output lenses and said sample system, comprising separate parameterized equations for independently calculating retardance entered between orthogonal components of a beam of electromagnetic radiation caused to pass through each of said converging input and diverging output lenses and interact with said sample system in a plane of incidence thereto; such that where parameters in said mathematical model are properly evaluated, retardance entered between orthogonal components of a beam of electromagnetic radiation which passes through each of said converging input and diverging output lenses and interacts with said sample system in a plane of incidence thereto can be independently calculated from said parameterzed equations, given wavelength;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said converging input lens, interact with said parameterizable sample system in a plane of incidence thereto, and exit through said diverging output lens and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input converging lens, interact with said sample system in a plane of incidence thereto, and exit through said diverging output lens.

The end result of practice of said method is that application of said parameterized equations for each of said converging input lens, diverging output lens and sample system for which values of parameters therein have been determined in step f., enables independent calculation of retardance entered between orthogonal components of a beam of electromagnetic radiation by each of said converging input and diverging output lenses, and said sample system, at given wavelengths in said spectroscopic set of ellipsometric data. And, it is emphasized that said calculated retardance values for each of said converging input lens, output diverging lens and sample system are essentially uncorrelated.

As further discussed supra herein, a modification to the just recited method can be to, (in the step d. provision of a mathematical model for said ellipsometer system and said input and diverging output lenses and said parameterizable sample system for each of said converging input and diverging output lenses), provide separate parameterized mathematical model parameterized equations for retardance entered to each of said two orthogonal components of a beam of electromagnetic radiation caused to pass through said converging input and diverging output lenses. When this is done, at least one of said orthogonal components for each of said input converging and diverging output lenses is directed out of the plane of incidence of said electromagnetic beam onto said parameterizable sample system. And, typically, though not necessarily, one orthogonal component will be aligned with the plane of incidence of said electromagnetic beam onto said parameterizable sample system. When this is done, calculation of retardation entered between orthogonal components of said beam of electromagnetic radiation, given wavelength, by said input converging lens is provided by comparison of retardance entered to each of said orthogonal components for said converging input lens, and such that calculation of retardation entered between orthogonal components of said beam of electromagnetic radiation, given wavelength, by said diverging output lens is provided by comparison of retardance entered to each of said orthogonal components for said diverging output lens.

It is pointed out that the step f. simultaneous evaluation of parameters in said mathematical model parameterized equations for said parameterizable sample system, and for said converging input diverging output lenses, is typically, though not necessarily, achieved by a square error reducing mathematical curve fitting procedure.

It is important to understand that in the method recited infra, the step b. positioning of an ellipsometer system source of electromagnetic radiation and an ellipsometer system detector system includes positioning a polarizer between said source of electromagnetic radiation and said converging input lens, and the positioning of an analyzer between said diverging output lens and said detector system, and in which the step e. obtaining of a spectroscopic set of ellipsometric data typically involves obtaining data at a plurality of settings of at least one component selected from the group consisting of: (said analyzer and said polarizer). As well, it is to be understood that additional elements can also be placed between said source of electromagnetic radiation and said converging input lens, and/or between said diverging output lens and said detector system, and that the step e. obtaining of a spectroscopic set of ellipsometric data can involve, alternatively or in addition to the recited procedure, obtaining data at a plurality of settings of at least one of said additional components.

It is also to be understood that the step of providing separate parameterized mathematical model parameterized equations for enabling independent calculation of retardance entered by said converging input said diverging output lenses between orthogonal components of a beam of electromagnetic radiation caused to pass through said converging input and diverging output lenses, and by said sample system, preferably involves parameterized equations having a form selected from the group consisting of:

$$ret(\lambda)=(K1/\lambda)$$

$$ret(\lambda)=(K1/\lambda)*(1+(K2/\lambda))$$

$$ret(\lambda)=(K1/\lambda)*(1+(K2/\lambda)+(K3/\lambda^4))$$

A modified method of accurately evaluating parameters in parameterized equations in a mathematical model of a system of spatially separated converging input and diverging output lenses, said parameterized equations enabling, when parameters therein are properly evaluated, independent calculation of retardation entered by each of said input converging lens and said output lens to at least one orthogonal component(s) of a beam of electromagnetic radiation caused to pass through said converging input and diverging output lenses, at least one of said converging input and diverging output lenses being birefringent, said method comprising, in a functional order, the steps of:

a. providing spatially separated converging input and diverging output lenses, at least one of said converging input and diverging output lenses demonstrating birefringence when a beam of electromagnetic radiation is caused to pass therethrough, there being a means for supporting a sample system positioned between said converging input and diverging output lenses;

b. positioning an ellipsometer system source of electromagnetic radiation and an ellipsometer system detector system such that in use a beam of electromagnetic radiation provided by said source of electromagnetic radiation is caused to pass through said converging input lens, interact with said sample system in a plane of incidence thereto, and exit through said diverging output lens and enter said detector system;

c. providing a sample system to said means for supporting a sample system;

d. providing a mathematical model for said ellipsometer system and said converging input and diverging output lenses and said sample system, comprising, for each of said input converging lens and said diverging output lens, separate parameterized equations for retardance for at least one orthogonal component in a beam of electromagnetic radiation provided by said source of electromagnetic radiation, which orthogonal component is directed out of a plane of incidence which said electromagnetic beam makes with said sample system in use, and optionally providing separate parameterized equations for retardance for an in-plane orthogonal component of said beam of electromagnetic radiation, such that retardation entered to said out-of-plane orthogonal component, and optionally to said in-plane orthogonal component, of said beam of electromagnetic radiation by each of said converging input and diverging output lenses, can, for each of said converging input and diverging output lenses, be separately calculated by said parameterized equations, given wavelength, where parameters in said parameterized equations are properly evaluated;

e. obtaining a spectroscopic set of ellipsometric data with said sample system present on the means for supporting a sample system, utilizing a beam of electromagnetic radiation provided by said source of electromagnetic radiation, said beam of electromagnetic radiation being caused to pass through said input lens, interact with said sample system in a plane of incidence thereto, and exit through said diverging output lens and enter said detector system;

f. by utilizing said mathematical model provided in step d. and said spectroscopic set of ellipsometric data obtained in step e., simultaneously evaluating sample system DELTA'S in correlation with in-plane orthogonal component retardation entered to said beam of electromagnetic radiation by each of said input converging and diverging output lenses, and parameters in said mathematical model parameterized equations for out-of-plane retardance entered by said converging input lens and said output lens to a beam of electromagnetic radiation caused to pass through said input lens, interact with said sample system in said plane of incidence thereto, and exit through said output lens.

Again, application of said parameterized equations for out-of-plane retardance entered by said converging input lens and said diverging output lens to a beam of electromagnetic radiation caused to pass through said converging input lens, interact with said sample system in said plane of incidence thereto, and exit through said diverging output lens, for which values of parameters therein are determined in step f., enables independent calculation of retardance entered to said out-of-plane orthogonal component of a beam of electromagnetic radiation by each of said converging input and diverging output lenses, given wavelength.

Also, again the step f. simultaneous evaluation of parameters in said mathematical model parameterized equations for calculation of retardance entered to said out-of-plane orthogonal component of a beam of electromagnetic radiation by each of said converging input and diverging output lenses, given wavelength, and said correlated sample system DELTA'S and retardance entered to said in-plane orthogonal component of a beam of electromagnetic radiation by each of said input converging and diverging output lenses, is typically achieved by a square error reducing mathematical curve fitting procedure.

It remains, in the presently disclosed method, to provide values for parameters in the in-plane parameterized equations for retardation, in said mathematical model of a system of spatially separated converging input and diverging output lenses. The presently disclosed method threfore further comprises the steps of:

g. providing a parameterized equation for retardation entered by said sample system to the in-plane orthogonal component of a beam of electromagnetic radiation, and as necessary similar parameterized equations for retardation entered by each of said converging input and diverging output lenses to the in-plane orthogonal component of a beam of electromagnetic radiation; and h. by utilizing said parameterized mathematical model provided in step d. and said spectroscopic set of ellipsometric data obtained in step e., simultaneously evaluating parameters in said mathematical model parameterized equations for independent calculation of retardance entered in-plane by said sample system and by said converging input lens and said diverging output lens such that the correlation between sample system DELTA'S and the retardance entered by said in-plane orthogonal component of a beam of electromagnetic radiation by each of said input converging and diverging output lenses, at given wavelengths in said spectroscopic set of ellipsometric data, is broken.

The end result of practice of the immediately foregoing steps a.–h. is that application of said parameterized equations for each of said converging input lens, diverging output lens and sample system for which values of parameters therein have been determined in step h., enables independent calculation of retardance entered to both said out-of-plane and said in-plane orthogonal components of a beam of electromagnetic radiation by each of said converging input and diverging output lenses, and retardance entered by said sample system to said in-plane orthogonal component of said beam of electromagnetic radiation, at given wavelengths in said spectroscopic set of ellipsometric data.

As before for other parameter evaluation steps, the step h. simultaneous evaluation of parameters in said mathematical model parameterized equations for said in-plane retardation entered by said parameterized sample system, and said converging input and diverging output lenses, is typically achieved by a square error reducing mathematical curve fitting procedure.

If the sample system present can not be easily parameterized, the presently disclosed method of accurately evaluating parameters in parameterized equations in a mathematical model of a system of spatially separated input converging and diverging output lenses, provides that the following steps, g.–j. be practiced:

g. removing the sample system from said means for supporting a sample system positioned between said converging input and diverging output lenses, and positioning in its place an alternative sample system for which a parameterized equation for calculating in-plane retardance entered to a beam of electromagnetic radiation, given wavelength, can be provided;

h. providing a parameterized equation for retardation entered in-plane to an orthogonal component of a beam of electromagnetic radiation by said alternative sample system which is then positioned on said means for supporting a sample system positioned between said converging input and diverging output lenses, and as necessary similar parameterized equations for retardation entered by each of said input converging and diverging output lenses to the in-plane orthogonal component of a beam of electromagnetic radiation;

i. obtaining a spectroscopic set of ellipsometric data with said alternative sample system present on the means for supporting a sample system, utilizing a beam of electromagnetic radiation provided by said source of electromagnetic radiation, said beam of electromagnetic radiation being caused to pass through said converging input lens, interact with said alternative sample system in a plane of incidence thereto, and exit through said diverging output lens and enter said detector system;

j. by utilizing said parameterized mathematical model for said converging input lens and said diverging output lens provided in step d. and said parameterized equation for retardation entered by said alternative sample system provided in step h., and said spectroscopic set of ellipsometric data obtained in step i., simultaneously evaluating parameters in said mathematical model parameterized equations for independent calculation of retardance entered to an in-plane orthogonal component of said beam of electromagnetic radiation by said alternative sample system and by said converging input lens and said diverging output lens, such that correlation between DELTA'S entered by said alternative sample system and retardance entered by said in-plane orthogonal component of said beam of electromagnetic radiation, by each of said converging input and diverging output lenses, at given wavelengths in said spectroscopic set of ellipsometric data, is broken, said simultaneous evaluation optionally providing new values for parameters in parameterized equations for calculation of retardance entered in said out-of-plane components of said beam of electromagnetic radiation by each of said converging input lens and said diverging output lens;

The end result being that application of said parameterized equations for each of said converging input lens and diverging output lens and alternative sample system, for each of which values of parameters therein have been determined in step j., enables independent calculation of retardance entered to both said out-of-plane and said in-plane orthogonal components of a beam of electromagnetic radiation by each of said input converging lens and said diverging output lens, and retardance entered by said alternative sample system to said in-plane orthogonal component of a beam of electromagnetic radiation, at given wavelengths in said spectroscopic set of ellipsometric data.

As before, said presently disclosed method of accurately evaluating parameters in parameterized equations in a mathematical model of a system of spatially separated input converging and diverging output lenses provides that in the step j. simultaneous evaluation of parameters in said mathematical model parameterized equations for said in-plane retardance entered by said parameterized sample system, and at least said in-plane input lens and diverging output lens, is typically achieved by a square error reducing mathematical curve fitting procedure.

As mentioned with respect to the first method of the present invention disclosed herein, the presently disclosed method of accurately evaluating parameters in parameterized equations in a mathematical model of a system of spatially separated input converging and diverging output lenses provides that the step b. positioning of an ellipsometer system source of electromagnetic radiation and an ellipsometer system detector system includes positioning a polarizer between said source of electromagnetic radiation and said converging input lens, and the positioning of an analyzer between said diverging output lens and said detector system, and in which the step e. obtaining of a spectroscopic set of ellipsometric data involves obtaining data at a plurality of settings of at least one component selected from the group consisting of: (said analyzer and said polarizer). As well, it is again to be understood that additional elements can also be placed between said source of electromagnetic radiation and said converging input lens, and/or between said diverging output lens and said detector system, and that the step e. obtaining of a spectroscopic set of ellipsometric data can involve, alternatively or in addition to the recited procedure, obtaining data at a plurality of settings of at least one of said additional components.

Said presently disclosed method of accurately evaluating parameters in parameterized equations in a mathematical model of a system of spatially separated converging input and diverging output lenses also provides that the step of providing separate parameterized mathematical model parameterized equations for enabling independent calculation of out-of-plane and in-plane retardance entered by said converging input said diverging output lenses to said beam of electromagnetic radiation caused to pass through said input and diverging output lenses, and that retardance entered by a parameterized sample system, involve parameterized equations having a form selected from the group consisting of:

$$ret(\lambda)=(K1/\lambda)$$
$$ret(\lambda)=(K1/\lambda)*(1+(K2/\lambda^2))$$
$$ret(\lambda)=(K1/\lambda)*(1+(K2/\lambda^2)+(K3/\lambda^4))$$

It is again noted that while the present invention can be practiced with any type "lenses", be there one or two of them, (ie. one of the input or diverging output lenses can be essentially non-birefringent and even ambient), and while an converging input lens or diverging output lens can be considered to be a compoiste formed by a plurality of elements, (eg. a compensator and a polarizer), the step a. providing of spatially separated converging input and diverging output lenses is best exemplified as being practiced by the providing of an ellipsometer system that has both converging input and diverging output lenses present therein through which an beam of electromagnetic radiation is caused to enter and exit, repectively.

Any method of the present invention can further involve, in a functional order the following steps a1.–a4:

a1. fixing evaluated parameter values in mathematical model parameterized equations, for each of said converging input lens and diverging output lens, such that said parameterized equations allow independent determination of retardation entered between orthogonal components of a beam of electromagnetic radiation caused to pass through said converging input and diverging output lenses, given wavelength; and a2. causing an unknown sample system to be present on said means for supporting a sample system;

a3. obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said converging input lens, interact with said alternative sample system in a plane of incidence thereto, and exit through said diverging output lens and enter said detector system; and a4. by utilizing said mathematical model for said input converging lens and said diverging output lens in which parameter values in mathematical model parameterized equations, for each of said converging input lens and diverging output lens have been fixed, simultaneously evaluating PSI'S and uncorrelated DELTA'S parameters for said unknown sample system.

As in other steps in the present invention method in which parameter values are evaluated, it is again noted that the method of accurately evaluating parameters in parameterized equations in a mathematical model of a system of spatially separated input converging and diverging output lenses in which said simultaneous evaluation of PSI'S and DELTA'S for said unknown sample are typically achieved by a square error reducing mathematical curve fitting procedure.

As alluded to earlier, the step of providing spatially separated converging input and diverging output lenses, at least one of said converging input and diverging output lenses demonstrating birefringence when a beam of electromagnetic radiation is caused to pass therethrough, can involve one lens is not birefringent. And, said one lens which is not birefringent can be essentially a surrounding ambient, (ie. a phantom lens which is essentially just the atmosphere surrounding a sample system).

It is noted that where parameters in parameterized equations for out-of-plane retardance equations have been determined, a focused version of the present invention method for accurately evaluating parameters in parameterized equations in a mathematical model of a system of spatially separated input converging and diverging output lenses can comprise the steps of b1–b7:

b1. fixing evaluated parameter values in mathematical model parameterized equations, for each of said converging input lens and diverging output lens, such that said parameterized equations allow independent determination of retardation entered between orthogonal components of a beam of electromagnetic radiation caused to pass through said converging input and diverging output lenses, given wavelength; and b2. causing an unknown sample system to be present on said means for supporting a sample system;

b3. obtaining a spectroscopic set of ellipsometric data with said unknown sample system present on the means for supporting a sample system, utilizing a beam of electromagnetic radiation provided by said source of electromagnetic radiation, said beam of electromagnetic radiation being caused to pass through said converging input lens, interact with said alternative sample system in a plane of incidence thereto, and exit through said diverging output lens and enter said detector system; and b4. by utilizing said mathematical model for said input converging lens and said diverging output lens in which parameter values in mathematical model parameterized equations, for each of said converging input lens and diverging output lens have been fixed, simultaneously evaluating ALPHA'S and BETA'S for said unknown sample system;

b5. applying transfer functions to said simultaneously evaluated ALPHA'S and BETA'S for said unknown sample system to the end that a data set of effective PSI's and DELTA's for a combination of said lenses and said sample system is provided;

b6. providing a mathematical model for said combination of said lenses and said sample system which separately accounts for the retardation effects of the presence of said lenses and said sample system by parameterized equations; and b7. by utilizing said mathematical model for said combination of said lenses and said sample system which separately accounts for the effects of the presence of at least said lenses by parameterized equations; and said data set of effective PSI's and DELTA's for a combination of said lenses and said sample system, simultaneously evaluating actual PSI's and DELTA's for said unknown sample system per se.

In the case, for instance, where the ellipsometer involved is a Rotating Analyzer, or Rotating Polarizer ellipsometer system, (but not where the ellipsometer involved is a Rotating Compensator System), it is noted that determination of "handedness" is required. Therefore the foregoing method can include, as necessary, providing a mathematical model for said combination of said lenses and said sample system which separately accounts for the retardation effects of the presence of said lenses and said sample system by parameterized equations which further includes providing for the effects of handedness. It is specifically stated that where the present invention approach of regressing onto effective PSI and DELTA values, (as determined in step b7.), is utilized, the mathematical modle can be derived so that "handedness" is accounted for in arriving at actual PSI's and DELTA's for said unknown sample system per se.

As a general comment it is to be understood that separate PSI and DELTA values are achieved for each angle of incidence a beam of electromagnetic radiation makes with respect to a sample substrate and for each wavelength utilized in a spectroscopic range of wavelengths.

It is noted that the terminology "Converging Input" and "Diverging Output" used throughout this Specification and Claims refers to the effect an Input Lens or Output Lens has on a beam of electromagnetic radiation. Ideally said language should be replaced with "Input Lens Assembly" and "Output Lens Assembly" respectfully.

The present invention will be better understood by reference to the Detailed Description Section of this Disclosure, with appropriate reference being has to the Drawings.

SUMMARY OF THE INVENTION

It is a primary objective and/or purpose of the present invention to describe a system which enables practice of focused beam small-spot spectroscopic ellipsometry over a large wavelength range, includeing into the deep UV, (eg. wavelengths down to and below 190 NM). Multi-element lenses which comrpise elements made of different materials allow essentially the same focal length to be achieved over a wavelength range.

It is another primary objective and/or purpose of the present invention to provide methods, (as originally presented in co-pending application Ser. No. 09/162,217 as regards compensating Vacuum Window Birefringence), for essentially eliminating birefringence achromatic effects of multiple element input and output lenses, (optionally in combination with other ellipsometrically indistinguishable elements), in the analysis of ellipsometric data obtained utilizing an ellipsometer system beam of electromagnetic radiation which passes through said lenses.

BRIEF DESCRIPTION OF THE DRAWINGS

FIG. 1a1, a general elemental configuration of an ellipsometer system which can be applied to investigate a sample system (SS).

FIG. 1a2 shows the construction of a quasi-achromatic multi-element lens which can be considered as present at AC1 or AC2.

FIG. 1a3 shows a perspective view of another ellipsometer system configuration showing the presence of electromagnetic beam directing optical elements (PRI) and (PRO).

FIG. 1b shows a side elevational view of a present invention system in the region of a material system.

FIG. 1c shows a top elevational view of a present invention system in the region of the detector.

FIG. 2 shows a top view of a present invention system showing the presence of optical elements (PRI) and (PRO).

DETAILED DESCRIPTION

Turning now to the Drawings, there is shown in FIG. 1a1, a general elemental configuration of an ellipsometer system which can be applied to investigate a sample system (SS). Shown are, sequentially:

a. a Source of a beam electromagnetic radiation (LS);
b. a Polarizer element (P);
c. optionally a compensator element (C1);
d. (additional element(s)) (AC1);
e. a sample system (SS);
f. (additional element(s)) (AC2);
g. optionally a compensator element (C2);
h. an Analyzer element (A); and
i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the present invention Disclosure, converging input diverging output lenses. FIG. 1a2 shows the construction of a quasi-achromatic multi-element lens which can be considered as present at AC1 or AC2. Note the presence of two lens elements (FE1), (FE2) and (FE3). (Note FE2 is air gap).

Figure 3A:
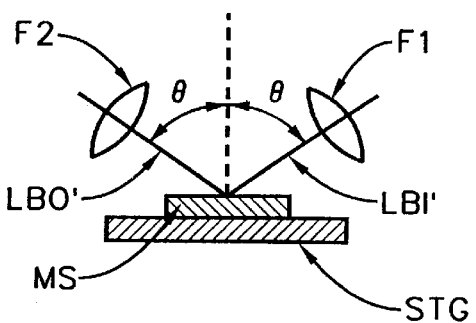
FIG. 3a shows a partial front elevational view of a present invention system.
Figure 3B:
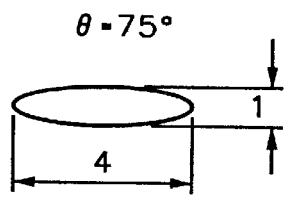
FIG. 3b shows a relative electromagnetic beam "Spot" size where an angle of incidence of seventy-five (75) degrees is utilized.

Another embodiment of the present invention System is shown in FIGS. 1a3, 2 and 3a. FIG. 1a3 shows a Perspective view of a present invention system, FIG. 2 is a Top View, and FIG. 3a is a Front Elevational View. FIG. 1a3 shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Material System (MS) present on a Material System supporting Stage (STG). FIGS. 1a3 and 2 show that said interaction with the Surface (S) of said Material System (MS) causes a generally vertically oriented Polarized Beam of Electromagnetic Radiation (LBO') to pass through Focusing Optic (F2). FIGS. 1a3 and 2 show that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Material System (MS). The Re-Collimated generally vertically oriented Beam of Electromagnetic Radiation (LBI') being identified as generally horizontally oriented Beam of Electromagnetic Radiation (LBO) after it has been caused to interact with Prism (PRO). FIG. 1b shows a side elevational view of the present invention system shown in FIG. 1a3, in the region of the Material System (MS). Note that the dashed line (S') indicates that varying Surface (S) region alignment is possible, and that such has an effect on the Angle-Of-Incidence at which the generally vertically oriented Polarized Beam of Electromagnetic Radiation (LBO') approaches the totally reflecting surface in Optical Element (PRO). FIG. 1c shows a more detailed, Top View, of a present invention Detector (DET) system as indicated in FIG. 1a3.

It is noted that (PRI) and (PRO) can be made of the same material, but the preferred embodiment provides that (PRI) be made of BK7 (refractive index approximately 1.55) and that (PRO) be made of F2 (refractive index approximately 1.7). For general interest, note that FIGS. 7 and 8 show sensitivity of DELTA to change in Angle-Of-Incidence (AOI) for F2 and BK7 Glass, respectively.

For demonstration purposes, FIG. 2 also shows, in dotted line form, Compensators (C) and (C'). When present one or more present Compensator(s) can be caused to rotate in use and the system is then a Rotating Compensator System and while obtaining data, both Polarizer (P) and Analyzer (A) are then held stationary. However, the Compensator(s) (C) and (C') can be absent or held stationary in use, and in use at least one of the Polarizer (P) and Analyzer (A) elements caused to rotate, thereby forming a Rotating Polarizer and/or Rotating Analyzer System. For the purposes of the present invention the specific element caused to rotate, or which is rotatable, in use is not a primary focus of Patentability. Rather, it is the presence of Total Internal Reflectance effecting Optical Elements (PRI) and (PRO) which characterize the present invention. (It is also to be understood that the (C) and (C') can be interpreted to identify Modulator Elements in a Modulation Element Ellipsometer System).

Figure 3C:
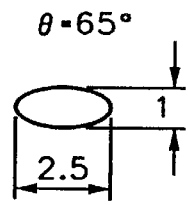
FIG. 3c shows a relative electromagnetic beam "Spot" size where an angle of incidence of sixty-five (65) degrees is utilized.

FIG. 3a shows that as viewed in frontal elevation, generally vertically oriented Polarized Beams of Electromagnetic Radiation (LBI') and (LBO') approach and are reflected from, respectively, Material System (MS) at equal angles of Incidence and Reflection (θ) with respect to a normal to the upper surface of said Material System (MS). It is to be noted, as demonstrated by FIG. 3b, that a generally vertically oriented Polarized Beam of Electromagnetic Radiation (LBI') caused to be incident on a Material System (MS) at Seventy-Five (75) Degrees, (a typical Brewster Angle for Semiconductors), will "Spread" so that relative dimensions of the Beam "Spot" caused to appear on said Material System (MS) are One (1) by Four (4). Where the Angle of Incidence is set to Sixty-Five (65) Degrees, FIG. 3c shows that the Spot size in shown to have relative dimensions of One (1) by Two and one-half (2.5). This demonstrates that the closer to a Normal Angle of Incidence, (eg. (θ)=zero (0.0) Degrees), with respect to a Material System (MS) surface), a generally vertically oriented Polarized Beam of Electromagnetic Radiation (LBI') is caused to assume, the more "Concentrated" will be the Beam Intensity, and the smaller will be the Material System Investigating Spot Size. Higher Beam Intensity and Reduced Material System Investigating Spot Size are often both desirable features, and can be easily achieved utilizing the present invention system without difficult Light Source (LS) and Detector (DET) alignment being required.

Continuing, a shortcomming of Rotating Element Ellipsometer Systems, (other than Rotating Compensator Ellipsometers), generally is that certain Magnitudes of well known Material System characterizing PSI or DELTA can not be monitored thereby. For instance, in Rotating Analyzer Ellipsometer Systems, Material Systems with DELTA near zero (0.0) or one-hundred-eighty (180) Degrees can not be measured. It is also noted that Thin Dielectric Films, such as Nitride and Oxide on semiconductor substrates, often present with a DELTA of one-hundred-eighty (180) Degrees at Angle of Incidence of less than the Brewster Angle, (eg. sixty-five (65) Degrees). The present invention recognizes this problem and can utilize first and/or second Optical Elements, (eg. Prisms), (PRI) and (PRO) which effect Phase Angle Retardation between "P" and "S" Orthogonal Components of a Polarized Beam of Electromagnetic Radiation caused to pass therethrough. (Note that a "P" Component of a Polarized Beam of Electromagnetic Radiation is that Component found to be in a Plane containing both an Incident Beam of Electromagnetic Radiation and a Normal to a Material System Surface, while an "S" Component is that Component perpendicular to said "P" Plane and Parallel to the Material System Surface). The Phase Angle Retardation between "P" and "S" Orthogonal Components of a Polarized Beam of Electromagnetic Radiation caused to pass therethrough can be caused to Nominally Forty-Five (45) Degrees for each Optical Element (PRI) and (PRO) shown in FIG. 2, for a total of a Nominal Ninety (90) Degrees. This added Retardation between "P" and "S" Orthogonal Components serves to shift the Material System DELTA's which a Rotating Analyzer Ellipsometer will be unable to measure to Ninety (90) and Two-Hundred-Seventy (270) Degrees. Again, most Thin Film Material Systems present a DELTA of near zero (0.0) and one-hundred-eighty (180) Degrees, hence the first and second Optical Elements (PRI) and (PRO) serve not only to direct a Polarized Beam of Electromagnetic Radiation as desired, but also serve to "Condition" said Polarized Beam of Electromagnetic Radiation so that it can be utilized to measure Material System DELTA's which are in the range of near zero (0.0) Degrees or near one-hundred-eighty (180) degrees.

Continuing, while FIG. 2 shows each of the first and second Optical Elements (PRI) and (PRO) as providing a total internal reflection angle of ninety (90) degrees, so as to direct said generally vertically oriented Incident Polarized Beam of Electromagnetic Radiation (LBI') at Ninety (90) Degrees with respect to said generally horizontally oriented Polarized Beam of Electromagnetic Radiation (LBI), and so as to direct said generally horizontally oriented Polarized Beam of Electromagnetic Radiation (LBO) at Ninety (90) Degrees with respect to said generally vertically oriented Polarized Beam of Electromagnetic Radiation (LBO'), other Optical Elements which provide other Angles between Incident and internally Reflected Beams of Electromagnetic Radiation can also be adapted for use in the present invention, and said usage is within the scope of the present invention. In such a case the terminology "generally horizontally oriented" and "other than generally horizontally oriented" serves to describe the relationship between incident and reflected beams of electromagnetic radiation. As well, Optical Elements which introduce other than essentially forty-five (45) degrees of retardation between "P" and "S" components of a Polarized Beam of Electromagnetic Radiation at a point of total internal reflection can be utilized. For instance, in a Rotating Compensator Ellipsometer System, as close to zero (0.0) degrees of entered retardation at a reflection as is possible might be desirable.

It should also be recognized that the presence of first and second Optical Elements (PRI) and (PRO) allow realization of a more laterally compact Ellipsometer or Polarimeter System Design, in that, as shown In FIG. 2, the Source of Electromagnetic Radiation (LS) and Detector (DET) can be placed as shown, rather than to the Right and Left of the Material System (MS) as is typical in most Ellipsometer Systems.

Figure 4A:
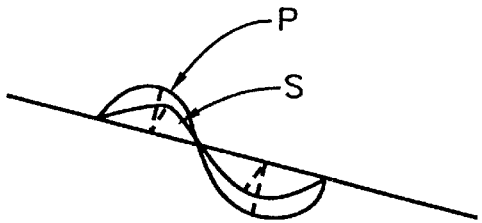
FIG. 4a shows "in-phase" components of a polarized beam of electromagnetic radiation.
Figure 4B:
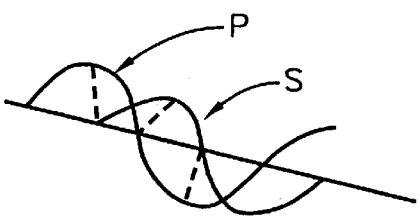
FIG. 4b shows "ninety-degree-out-of-phase" components of a polarized beam of electromagnetic radiation.

FIGS. 4a and 4b show "P" and "S" Components of a Polarized Beam of Electromagnetic Radiation for both "In-Phase" and "Ninety (90) Degrees Retardation" therebetween, respectively.

Figure 5:
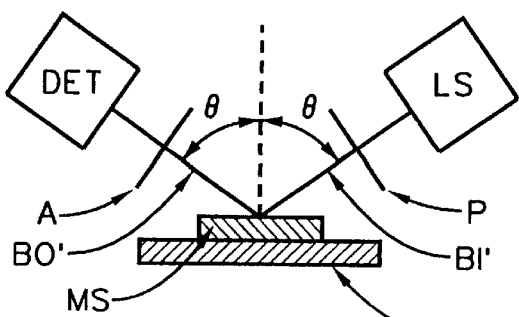
FIG. 5 shows a conventional prior art ellipsometer system.

FIG. 5 is included to provide a reference to conventional ellipsometer and polarimeter and the like Material System investigation systems reported in the prior art. Note that a Light Source (LS), Polarizer (P), Material System (MS) Analyzer (A) and Detector (DET) are shown, as well as Incident (BI') and Reflected (BO') Electromagnetic Radiation Beams, (which are respectively, analogically, similarly positioned as are (LBI') and (LBO') in FIG. 3a). The region of FIG. 5 in the vicinity of the Material System (MS) is very much like what is shown in FIG. 3a. However, the placement of the Light Source (LS) and Detector (DET) are shown to be necessarily very different from that shown in FIGS. 1a3 and 2, as the present invention first and second Optical Elements (PRI) and (PRO), shown in FIGS. 1a3 and 2, are not present. It is noted that adjustment of Light Source (LS) and Detector (DET) positioning to allow different Angles-of-Incidence (θ) to be achieved is inherently more difficult in a system fashioned after FIG. 5, than it is in a present invention system fashioned after FIGS. 1a3 and 2.

For purposes of applying the present invention methodology, in that as (PRI), (F1), (F2) and (PRO) remain stationary during use in data acquisition, it should be appreciated that the FIG. 1a3 (PRI) and Convergent Input Lens (F1) can be considered a composit system, as can (PRO) and divergent output lens (F2). The Claims should be interpreted to include ellipsometrically indistinguishable elements within the terminology "converging input lens" or "diverging output lens", where applicable.

Figure 6:
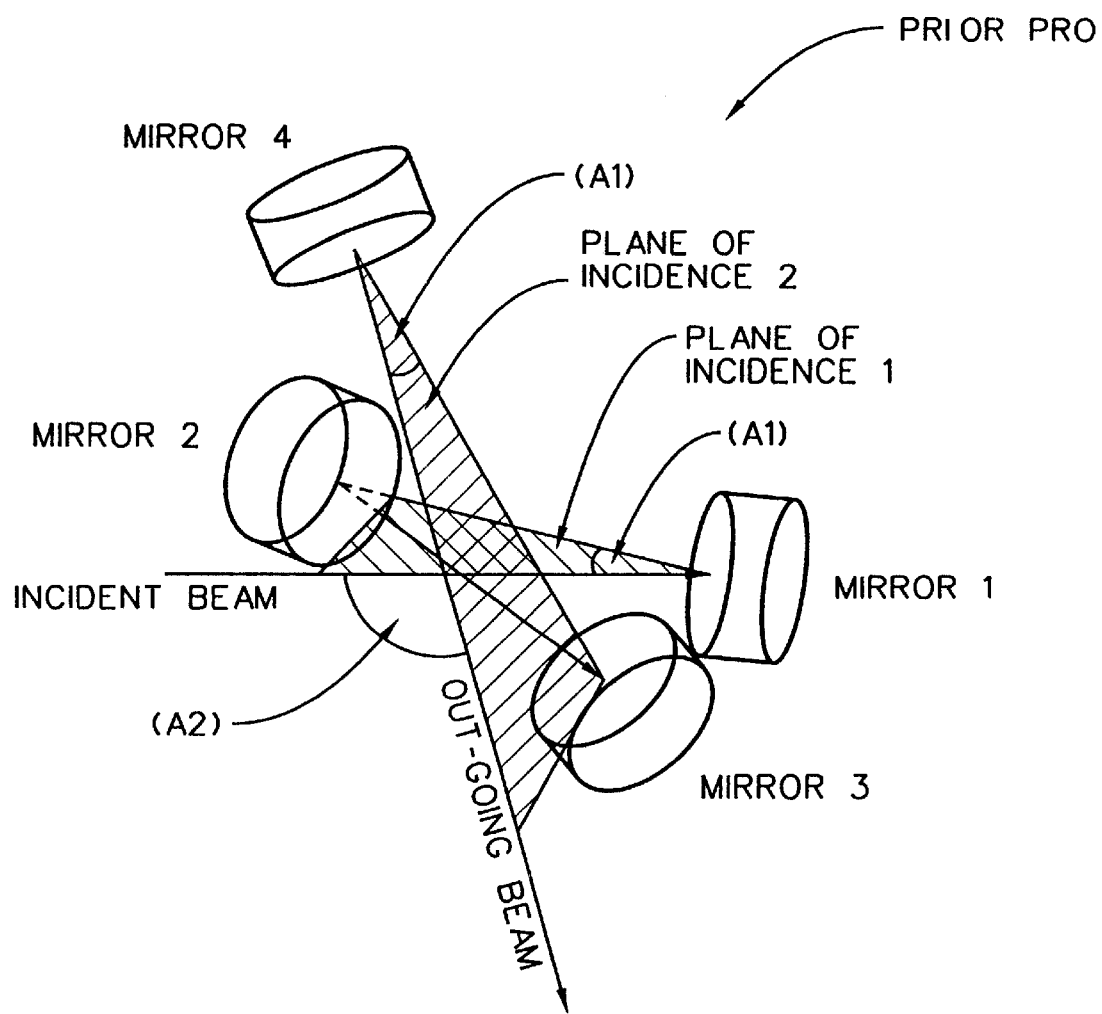
FIG. 6 shows a system, which can be used as (PRI) and/or (PRO), (shown in FIGS. 1a3 and 2), for changing the initial propagation direction of a beam of electromagnetic radiation without significantly changing the phase angle between orthogonal components thereof.

Also, Allowed but Copending application Ser. No. 09/144,764, filed Aug. 31, 1998, discloses specific beam folding optics in which specific (PRI) and (PRO) embodiments are decribed. Each of the (PRI) and (PRO) can comprise first and second systems which each comprise two pairs of reflecting means, between which first and second systems is positioned a sample system. FIG. 6 shows a system, which can be used as (PRI) and/or (PRO), for changing the initial propagation direction of a beam of electromagnetic radiation without significantly changing the phase angle between orthogonal components thereof, comprises two pairs of reflecting means, (MIRROR 1) and (MIRROR 2), oriented so that said initial beam of electromagnetic radiation (INCIDENT BEAM) reflects from a first reflecting means (MIRROR 1) in the first pair of reflecting means to a second reflecting means (MIRROR 2) in said first pair of reflecting means, in a first plane, (PLANE OF INCIDENCE 1), and such that the beam of electromagnetic radiation which reflects from said second reflecting means in said first pair of reflecting means is directed to a first reflecting means (MIRROR 3) in the second pair of said reflecting means, and reflects from said first reflecting means (MIRROR 3) in said second pair of reflecting means to a second reflecting means (MIRROR 4) in said second pair of reflecting means, in a second plane (PLANE OF INCIDENCE 2), which is essentially orthogonal to said first plane; such that the direction of propagation of the beam of electromagnetic radiation reflected from the second of the reflecting means in the second pair of reflecting means is different from the propagation direction of the initial beam of electromagnetic radiation; the basis of operation being that changes entered to the phase angle between orthogonal components of a beam of electromagnetic radiation by the first of said pairs of reflecting means are effectively canceled by said second pair of reflecting means.

Allowed but still Co-Pending application Ser. No. 09/162, 217 filed Sep. 29, 1998, and Allowed but Copending application Ser. No. 09/033,694 filed Mar. 3. 1998 provide additional insight, and Allowed but Copending application Ser. No. 09/144,764, filed Aug. 31, 1998 are incorporated hereinto by reference. In particular the 217 Application shows application of the present invention methodology, wherein vacuum chamber windows, at least one of which demonstrates bi-refringence, (instead of converging input and diverging output lenses), are investigated. The 694 Application provides experimental support for operational aspects of the FIG. 1a3 ellipsometer system configuration, and the 764 Application shows specific beam folding systems.

It remains only to disclose the mathematical basis for, and derivation of, the present invention second order mathematical model corrections, and said derivation requires the use of Matracies which represent the sample, and each element in the ellipsometer system.

To begin, as is disclosed in the 217 Application, it is to be understood that:

a beam of electromagnetic radiation from a source thereof can be mathematically modeled as a Stokes Vector:

Stokes vector for unpolarized input light:

$$I = \begin{bmatrix} 1 \\ 0 \\ 0 \\ 0 \end{bmatrix}$$

a polarization state insensitive detector can be mathematically modeled as a Stokes Vector:
Stoked vector for a polarization insensitive detector 'D': D=(1 0 0 0)

a Polarizer P, (or Analyzer A), can be mathematically modeled as Mueller Matrix:
Mueller Matrix for a polarizer 'P' or analyzer 'A'

$$P = \begin{bmatrix} 1 & 1 & 0 & 0 \\ 1 & 1 & 0 & 0 \\ 0 & 0 & 0 & 0 \\ 0 & 0 & 0 & 0 \end{bmatrix}$$

Azimuthal Rotation as a function of Angle ($\phi$) effected by an element can be modeled by a Mueller Matrix:
Azimuthal Rotation Mueller Matrix, as a function of angle '$\phi$'.

$$R(\phi) = \begin{bmatrix} 1 & 0 & 0 & 0 \\ 0 & \cos(2\phi) & \sin(2\phi) & 0 \\ 0 & -\sin(2\phi) & \cos(2\phi) & 0 \\ 0 & 0 & 0 & 1 \end{bmatrix}$$

a Compensator, Retarder or Bi-refrinent Window with a Retardance ($\delta$) can be mathematically modeled as:

$$W(\delta) = \begin{bmatrix} 1 & 0 & 0 & 0 \\ 0 & 1 & 0 & 0 \\ 0 & 0 & \cos(\delta) & \sin(\delta) \\ 0 & 0 & -\sin(\delta) & \cos(\delta) \end{bmatrix}$$

and a Sample can be mathematically modeled by a Mueller Matrix:
Mueller Matrix for a sample 'S':

$$S(\Psi, \Delta) = \begin{bmatrix} 1 & -N & 0 & 0 \\ -N & 1 & 0 & 0 \\ 0 & 0 & C & S \\ 0 & 0 & S & C \end{bmatrix}$$

where $N=\cos(2\Psi)$ $C=\sin(2\Psi)\cdot\cos(\Delta)$ $S=\sin(2\Psi)\cdot\sin(\Delta)$ A complete Mueller Matrix expresion for Signal Intensity out of a Rotating Analyzer ellipsometer system, without lenses (AC1) & (AC2) present, can then be written as:
Complete Mueller matrix expression for a rotating analyzer ellipsometer.

Signal_Intensity=$D\cdot(R(-\Omega_A)\cdot A\cdot R(\phi_A))\cdot S\cdot(R(-\phi_P)\cdot P\cdot R(\phi_P))\cdot I$ or more explicitly as:

$$(1\ 0\ 0\ 0) \cdot \begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} \cdot \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix} +$$

$$\begin{bmatrix} 1 & N & 0 & 0 \\ N & 1 & 0 & 0 \\ 0 & 0 & C & S \\ 0 & 0 & -S & C \end{bmatrix} \cdot \begin{bmatrix} 1 & 0 & 0 & 0 \\ 0 & \cos(2\phi P) & -\sin(2\phi P) & 0 \\ 0 & \sin(2\phi P) & \cos(2\phi P) & 0 \\ 0 & 0 & 0 & 1 \end{bmatrix} \cdot \begin{bmatrix} 1 & 1 & 0 & 0 \\ 1 & 1 & 0 & 0 \\ 0 & 0 & 0 & 0 \\ 0 & 0 & 0 & 0 \end{bmatrix} \cdot \begin{bmatrix} 1 & 0 & 0 & 0 \\ 0 & \cos(2\phi P) & -\sin(2\phi P) & 0 \\ 0 & \sin(2\phi P) & \cos(2\phi P) & 0 \\ 0 & 0 & 0 & 1 \end{bmatrix} \cdot \begin{bmatrix} 1 \\ 0 \\ 0 \\ 0 \end{bmatrix}$$

Multiplying this out provides:

Signal_Intensity=1−cos(2·φP)·N+(−N+cos(2·φP))·cos(2·φA)+sin(2·φA)·C·sin(2·φP)

and if the Analyzer (A) is rotating as a function of Time, (ie.φA=W*T), then the above Detector Intensity can be written as "DC" Normalized ellipsometric ALPHA (2w) and BETA (2w) Fourier Coefficients at (2w) frequency:

$$\alpha = \frac{\cos(2 \cdot \phi P) - N}{1 - \cos(2 \cdot \phi P) \cdot N}$$

$$\beta = \frac{\sin(2 \cdot \phi P) \cdot C}{1 - \cos(2 \cdot \phi P) \cdot N}$$

Where converging input and diverging output lenses (AC1) and (AC2) are present, and designated as (W1) and (W2) respectively, the Signal Intensity Equation becomes:

Signal_Intensity=
D·(R(-φ$_A$)·A·R(φ$_A$))·(R(·φ$_{W2}$)·W(δ2)·R(·φ$_{W2}$))·S·(R(·φ$_{W1}$)·W(δ1)·R(·φ$_{W1}$))·(R(φ$_P$)·P·R(φ$_P$))·I Re-evaluating the Rotating Analyzer and the Detector matricies provides:

First evaluate the Rotating Analyzer and Detector Matrices:

$$D \cdot (R(-\phi_A) \cdot A \cdot R(\phi_A)) = (1\ 0\ 0\ 0) \cdot$$

$$\begin{bmatrix} 1 & 0 & 0 & 0 \\ 0 & \cos(2\phi A) & -\sin(2\phi A) & 0 \\ 0 & \sin(2\phi A) & \cos(2\phi A) & 0 \\ 0 & 0 & 0 & 1 \end{bmatrix} +$$

$$\begin{bmatrix} 1 & 1 & 0 & 0 \\ 1 & 1 & 0 & 0 \\ 0 & 0 & 0 & 0 \\ 0 & 0 & 0 & 0 \end{bmatrix} +$$

-continued $$\begin{bmatrix} 1 & 0 & 0 & 0 \\ 0 & \cos(2\phi A) & \sin(2\phi A) & 0 \\ 0 & -\sin(2\phi A) & \cos(2\phi A) & 0 \\ 0 & 0 & 0 & 1 \end{bmatrix}$$

Det_Analzyer=(1 cos(2·φA) sin(2·φA) 0)xs$_{out}$x(s0 s1 s2 s3)

Therefore, the ALPHA (2φA) and BETA (2φA) the complete system can be determined by multiplying out the rest of the Mueller Matricies (excluding the Analyzer and Detector Matraicies), using:

$$\alpha = \frac{s1}{s0}$$

$$\beta = \frac{s2}{s0}$$

Multiplying out the rest of the Mueller Matricies, without any present invention simplifcation provides:

$$\begin{bmatrix} 1 & 0 & 0 & 0 \\ 0 & \cos2\phi w2 & -\sin2\phi w2 & 0 \\ 0 & \sin2\phi w2 & \cos2\phi w2 & 0 \\ 0 & 0 & 0 & 1 \end{bmatrix} \cdot \begin{bmatrix} 1 & 0 & 0 & 0 \\ 0 & 1 & 0 & 0 \\ 0 & 0 & \cos\delta w2 & \sin\delta w2 \\ 0 & 0 & -\sin\delta w2 & \cos\delta w2 \end{bmatrix} \cdot \begin{bmatrix} 1 & 0 & 0 & 0 \\ 0 & \cos2\phi w2 & \sin2\phi w2 & 0 \\ 0 & -\sin2\phi w2 & \cos2\phi w2 & 0 \\ 0 & 0 & 0 & 1 \end{bmatrix} \cdot \begin{bmatrix} 1 & -N & 0 & 0 \\ -N & 1 & 0 & 0 \\ 0 & 0 & C & S \\ 0 & 0 & -S & C \end{bmatrix} +$$

$$\begin{bmatrix} 1 & 0 & 0 & 0 \\ 0 & \cos2\phi w1 & -\sin2\phi w1 & 0 \\ 0 & \sin2\phi w1 & \cos2\phi w1 & 0 \\ 0 & 0 & 0 & 1 \end{bmatrix} \cdot \begin{bmatrix} 1 & 0 & 0 & 0 \\ 0 & 1 & 0 & 0 \\ 0 & 0 & \cos\delta w1 & \sin\delta w1 \\ 0 & 0 & -\sin\delta w1 & \cos\delta w1 \end{bmatrix} \cdot \begin{bmatrix} 1 & 0 & 0 & 0 \\ 0 & \cos2\phi w1 & \sin2\phi w1 & 0 \\ 0 & -\sin2\phi w1 & \cos2\phi w1 & 0 \\ 0 & 0 & 0 & 1 \end{bmatrix} \cdot \begin{bmatrix} 1 \\ \cos2\phi P \\ \sin2\phi P \\ 0 \end{bmatrix}$$

$$s = \begin{bmatrix} s0 \\ s1 \\ s2 \\ s3 \end{bmatrix}$$

and further:

s0=1−cos 2φP·N·cos 2 φw1$^2$−cos 2φP·N·sin 2φw1$^2$·cos δw1 . . . +−sin 2φP·N·cos 2φw1·sin 2φw1+sin 2φP·N·sin 2φw1·cos δw1·cos 2φw1

$$s1 = \begin{bmatrix} -N \cdot \cos2\phi w2^2 - N \cdot \sin2\phi w2^2 \cdot \cos\delta w2 + \cos2\phi P \cdot \cos2\phi w1^2 \cdot \cos2\phi w2^2 + \\ \cos2\phi P \cdot \cos2\phi w1^2 \cdot \sin2\phi w2^2 \cdot \cos\delta w2 + \\ \cos2\phi P \cdot \cos2\phi w1 \cdot \sin2\phi w1 \cdot C \cdot \cos2\phi w2 \cdot \sin2\phi w2 + \\ -\cos2\phi P \cdot \cos2\phi w1 \cdot \sin2\phi w1 \cdot C \cdot \sin2\phi w2 \cdot \cos2\delta w2 \cdot \cos\phi w2 + \\ \cos2\phi P \cdot \cos2\phi w1 \cdot \sin2\phi w1 \cdot \sin2\phi w2 \cdot \sin\delta w2 \cdot S + \\ \cos2\phi P \cdot \cos\delta w1 \cdot \sin2\phi w1^2 \cdot \cos2\phi w2^2 + \\ \cos2\phi P \cdot \cos\delta w1 \cdot \sin2\phi w1^2 \cdot \sin2\phi w2^2 \cdot \cos\delta w2 + \\ -\cos2\phi P \cdot \sin2\phi w1 \cdot \cos\delta w1 \cdot \cos2\phi w1 \cdot C \cdot \cos2\phi w2 \cdot \sin2\phi w2 + \\ \cos2\phi P \cdot \sin2\phi w1 \cdot \cos\delta w1 \cdot \cos2\phi w1 \cdot C \cdot \sin2\phi w2 \cdot \cos2\delta w2 \cdot \cos2\phi w2 + \\ -\cos2\phi P \cdot \sin2\phi w1 \cdot \cos\delta w1 \cdot \cos2\phi w1 \cdot \sin2\phi w2 \cdot \sin2\delta w2 \cdot S + \\ \cos2\phi P \cdot \sin2\phi w1 \cdot \sin\delta w1 \cdot S \cdot \cos2\phi w2 \cdot \sin2\phi w2 + \\ -\cos2\phi P \cdot \sin2\phi w1 \cdot \sin\delta w1 \cdot S \cdot \sin2\phi w2 \cdot \cos2\delta w2 \cdot \cos2\phi w2 + \\ -\cos2\phi P \cdot \sin2\phi w1 \cdot \sin\delta w1 \cdot \sin2\phi w2 \cdot \sin2\delta w2 \cdot C + \\ \sin2\phi P \cdot \sin2\phi w1 \cdot \cos2\phi w1 \cdot \cos2\phi w2^2 + \\ \sin2\phi P \cdot \sin2\phi w1 \cdot \cos2\phi w1 \cdot \sin2\phi w2^2 \cdot \cos\delta w2 + \\ \sin2\phi P \cdot \sin2\phi w1^2 \cdot C \cdot \cos2\phi w2 \cdot \sin2\phi w2 + \\ -\sin2\phi P \cdot \sin2\phi w1^2 \cdot C \cdot \sin2\phi w2 \cdot \cos\delta w2 \cdot \cos2\phi w2 + \\ \sin2\phi P \cdot \sin2\phi w1^2 \cdot \sin2\phi w2 \cdot \sin\delta w2 \cdot S + \\ -\sin2\phi P \cdot \cos2\phi w1 \cdot \cos\delta w1 \cdot \sin2\phi w1 \cdot \cos2\phi w2^2 + \\ -\sin2\phi P \cdot \cos2\phi w1 \cdot \cos\delta w1 \cdot \sin2\phi w1 \cdot \sin2\phi w2^2 \cdot \cos\delta w2 + \\ \sin2\phi P \cdot \cos2\delta w1 \cdot \cos2\phi w1^2 \cdot C \cdot \cos2\phi w2 \cdot \sin2\phi w2 + \\ -\sin2\phi P \cdot \cos\delta w1 \cdot \cos2\phi w1^2 \cdot C \cdot \sin2\phi w2 \cdot \cos\delta w2 \cdot \cos2\phi w2 + \\ \sin2\phi P \cdot \cos\delta w1 \cdot \cos2\phi w1^2 \cdot \sin2\phi w2 \cdot \sin\delta w2 \cdot S + \\ -\sin2\phi P \cdot \cos2\delta w1 \cdot \sin\delta w1 \cdot S \cdot \cos2\phi w2 \cdot \sin2\phi w2 + \\ \sin2\phi P \cdot \cos2\delta w1 \cdot \sin\delta w1 \cdot S \cdot \sin2\phi w2 \cdot \cos\delta w2 \cdot \cos2\phi w2 + \\ \sin2\phi P \cdot \cos2\phi w1 \cdot \sin\delta w1 \cdot \sin2\phi w2 \cdot \sin\delta w2 \cdot C \end{bmatrix}$$

$s2 = -\cos2\phi w2 \cdot \sin2\phi w2 \cdot N + \cos2\phi w2 \cdot \sin2\phi w2 \cdot N \cdot \cos\delta w2 +$ $\cos2\phi P \cdot \cos2\phi w1^2 \cdot \cos2\phi w2 \cdot \sin2\phi w2 +$ $-\cos2\phi P \cdot \cos2\phi w1^2 \cdot \sin2\phi w2 \cdot \cos\delta w2 \cdot \cos2\phi w2 +$ $-\cos2\phi P \cdot \cos2\phi w1 \cdot \sin2\phi w1 \cdot C \cdot \sin2\phi w2^2 +$ $\cos2\phi P \cdot \cos2\phi w1 \cdot \sin2\phi w1 \cdot C \cdot \cos2\phi w2^2 \cdot \cos\delta w2 +$ $-\cos2\phi P \cdot \cos2\phi w1 \cdot \sin2\phi w1 \cdot \cos2\phi w2 \cdot \sin\delta w2 \cdot S +$ $\cos2\phi P \cdot \cos\delta w1 \cdot \sin2\phi w1^2 \cdot \cos2\phi w2 \cdot \sin2\phi w2 +$ $-\cos2\phi P \cdot \cos\delta w1 \cdot \sin2\phi w1^2 \cdot \sin2\phi w2 \cdot \cos\delta w2 \cdot \cos2\phi w2 +$ $-\cos2\phi P \cdot \sin2\phi w1 \cdot \cos\delta w1 \cdot \cos2\phi w1 \cdot C \cdot \sin2\phi w2^2 +$ $-\cos2\phi P \cdot \sin2\phi w1 \cdot \cos\delta w1 \cdot \cos2\phi w1 \cdot C \cdot \cos2\phi w2^2 \cdot \cos\delta w2 +$ $\cos2\phi P \cdot \sin2\phi w1 \cdot \cos\delta w1 \cdot \cos2\phi w1 \cdot \cos2\phi w2 \cdot \sin\delta w2 \cdot S +$ $\cos2\phi P \cdot \sin2\phi w1 \cdot \sin\delta w1 \cdot S \cdot \sin2\phi w2^2 +$ $\cos2\phi P \cdot \sin2\phi w1 \cdot \sin\delta w1 \cdot S \cdot \cos2\phi w2^2 \cdot \cos\delta w2 +$ $\cos2\phi P \cdot \sin2\phi w1 \cdot \sin\delta w1 \cdot \cos2\phi w2 \cdot \sin\delta w2 \cdot C +$ $\sin2\phi P \cdot \sin2\phi w1 \cdot \cos2\phi w1 \cdot \cos2\phi w2 \cdot \sin2\phi w2 +$ $-\sin2P \cdot \sin2\phi w1 \cdot \cos2\phi w1 \cdot \sin2\phi w2 \cdot \cos\delta w2 \cdot \cos2\phi w2 +$ $\sin2\phi P \cdot \sin2\phi w1^2 \cdot C \cdot \sin2\phi w2^2 +$ $\sin2\phi P \cdot \sin2\phi w1^2 \cdot C \cdot \cos2\phi w2^2 \cdot \cos\delta w2 +$ $-\sin2\phi P \cdot \sin2\phi w1^2 \cdot \cos2\phi w2 \cdot \sin\delta w2 \cdot S +$ -continued $-\sin2\phi P \cdot \cos2\phi w1 \cdot \cos\delta w1 \cdot \sin2\phi w1 \cdot \cos2\phi w2 \cdot \sin2\phi w2 +$ $\sin2\phi P \cdot \cos2\phi w1 \cdot \cos\delta w1 \cdot \sin2\phi w1 \cdot \sin2\phi w2 \cdot \cos\delta w2 \cdot \cos2\phi w2 +$ $\sin2\phi P \cdot \cos\delta w1 \cdot \cos2\phi w1^2 \cdot C \cdot \sin2\phi w2^2 +$ $\sin2\phi P \cdot \cos\delta w1 \cdot \cos2\phi w1^2 \cdot C \cdot \cos2\phi w2^2 \cdot \cos\delta w2 +$ $-\sin2\phi P \cdot \cos\delta w1 \cdot \cos2\phi w1^2 \cdot \cos2\phi w2 \cdot \sin\delta w2 \cdot S +$ $-\sin2\phi P \cdot \cos2\phi w1 \cdot \sin\delta w1 \cdot S \cdot \sin2\phi w2^2 +$ $-\sin2\phi P \cdot \cos2\phi w1 \cdot \sin\delta w1 \cdot S \cdot \cos2\phi w2^2 \cdot \cos\delta w2 +$ $-\sin2\phi P \cdot \sin\delta w1 \cdot \cos2\phi w1 \cdot \cos2\phi w2 \cdot \sin\delta w2 \cdot C$ with ellipsometric ALPHA and BETA being given by:

$$\alpha = \frac{s1}{s0}$$

$$\beta = \frac{s2}{s0}$$

Now, the present invention simplification is mathematically based in the fact that input and output rotation matrices involve Sin and Cos of double the rotation angle imposed thereby, and that if an angle of forty-five (45) degrees is assumed for that rotation angle, then the $\sin(\theta)$ becomes 1.0, and the $\cos(\theta)$ becomes 0.0. This assumption is equivalent to saying that each of said input and output lenses effects two orthogonal components of a beam of electromagnetic radiation passed therethrough differently, and that one of said orthogonal components is oriented "In-The-Plane" of the beam of electromagnetic radiation as it interacts with a sample system, and that the other orthogonal component is oriented "Out-Of-The-Plane" of the beam of electromagnetic radiation as it interacts with a sample system. When this assumption is made, the following hold:
for the "In-Plane" orthogonal component:

for in-plane, cos 2φw1=cos 2φw2=1, sin 2φw1=sin 2φw2=0

$s0 = 1 - \cos 2\phi P \cdot N$ $s1 = \cos 2\phi P - N$ $s2 = ((-\cos \delta w1 \cdot \sin \delta w2 - \sin \delta w1 \cdot \cos \delta w2) \cdot S - (\cos \delta w1 \cdot \cos \delta w2 - \sin \delta w1 \cdot \sin \delta w2) \cdot C) \cdot \sin 2\phi P$ $s2 = \sin 2\phi P \cdot (\cos(\delta w1 + \delta w2) \cdot C - \sin(\delta w1 + \delta w2) \cdot S)$ $s2 = \sin 2\phi P \cdot \sin(2\Psi) \cdot \cos(\Delta + \delta w1 + \delta w2)$ $$\alpha = \frac{\cos 2\phi P - N}{1 - \cos 2\phi P \cdot N}$$

$$\beta = \frac{\sin 2\phi P \cdot \sin(2\Psi) \cdot \cos(\Delta + \delta w1 + \delta w2)}{1 - \cos 2\phi P \cdot N}$$

for the "Out-Of-Plane" orthogonal component:

for out-of-plane, cos2φw1=cos2φw2=0, sin2φw1=sin2φw2=1

$s0 = 1 - \cos 2\phi P \cdot N \cdot \cos \delta w$ $s1 = -N \cdot \cos \delta w2 - \cos 2\phi P \cdot \sin \delta w1 \cdot \sin \delta w2 \cdot C + \sin 2\phi P \cdot \sin \delta w2 \cdot S + \cos 2\phi P \cdot \cos \delta w1 \cdot \cos \delta w2$ $s2 = \cos 2\phi P \cdot \sin \delta w1 \cdot S + \sin 2\phi P \cdot C$ $$\alpha = \frac{N \cdot \cos \delta w2 - \cos 2\phi P \cdot \sin \delta w1 \cdot \sin \delta w2 \cdot C - \sin 2\phi P \cdot \sin \delta w2 \cdot S - \cos 2\phi P \cdot \cos \delta w1 \cdot \cos \delta w2}{1 - \cos 2\phi P \cdot N \cdot \cos \delta w1}$$

$$\beta = \frac{\cos 2\phi P \cdot \sin \delta w1 \cdot S + \sin 2\phi P \cdot C}{1 - \cos 2\phi P \cdot N \cdot \cos \delta w1}$$

It will be appreciated that the equations for ellipsometric ALPHA and BETA with the present invention simplifying assumption are greatly simplified as compared to the equations for ellipsometric ALPHA and BETA without the present invention simplifying assumption being made. In addition, said simplified equations for ellipsometric ALPHA and BETA provide second order mathematical model correction. And, said present invention second order mathematical model correction equations are of approximately the same level of complexity as are the equations which provide first order mathematical model correction, which, as found in the literature are:

$$\alpha = \frac{\cos 2\phi P - N}{1 - \cos 2\phi P \cdot N} + \frac{\sin 2\phi P \cdot \sin 2\phi w2 \cdot \delta w2 \cdot S}{1 - \cos 2\phi P \cdot N}$$

$$\beta = \frac{\sin 2\phi P \cdot \cos(\Delta + \cos 2\phi w2 \cdot \delta w2 + \cos 2\phi w1 \cdot \delta w1)}{1 - \cos 2\phi P \cdot N} + \frac{\sin 2\phi w1 \cdot \delta w1 \cdot \cos 2\phi P \cdot S}{1 - \cos 2\phi P \cdot N}$$

It is to be further understood that the present invention applies parameterized equations for retardance (Δ) of converging input and diverging output lenses, and for parameterizable sample systems, of the form:

Delta Offset($\lambda$)=DelOff1/$\lambda$(1+DelOff2/$\lambda^2$+DelOff3/$\lambda^4$)

As presented in the Disclosure of the Invention Section of this Disclosure, the present invention includes application of said parameterized equations for converging input and diverging output lens retardance, both in conjunction with, and without, the present invention simplifying assumption that converging input and diverging output lenses rotation matrices, which involve the Sin(2θ) and Cos(2θ) of double the rotation angle imposed thereby, have an angle of forty-five (45) degrees assumed for that rotation angle, so that the Sin becomes 1.0, and the Cos becomes 0.0. This assumption, it is to be understood, provides that each orthogonal component of a beam of electromagnetic radiation passing through bi-refringent converging input and diverging output lenses is to be treated separately, and that retardance entered between said orthogonal components by passage through an input and/or output lens is determined by a comparison of the separate effects on each of said orthogonal components. It is noted that while the present invention mathematical justification for the simplifying assumption is based upon assuming an angle of forty-five (45) degrees for the rotation angle imposed by a converging input or diverging output lens, so that the Sin becomes 1.0, and the Cos becomes 0.0, the concept behind the present invention simplifying assumption is that orthogonal components of a beam of electromagnetic radiation can be considered to each be separately represented by a parameterized retardance equation. When the assumption of angle of forty-five (45) degrees for the rotation angle is made, however, the result is that one orthogonal component is out of the plane of incidence of a beam of electromagnetic radiation which is caused to interact with a sample system, and one orthogonal component thereof is in said plane of incidence. This, of course, means that here a sample can not be provided a parameterized equation for retardance, correlation of retardance entered by the converging input and diverging output lenses "in-plane", and that of a sample system, will exist, and must be broken. Said "in-plane" correlation can be broken by providing a sample system that can be parameterized, and simultaneously evaluating parameters in it, and in parameterized equations for retardance of the converging input and diverging output lenses in a separate calibration procedure.

While the preceding approach works well for analyzing ellipsometric data acquired by a Rotating Analyzer or Rotating Polarizer ellipsometer system wherein lenses are present, it is further to be understood that in cases where it is important to extract "true" values for the PSI and DELTA of a sample system, (eg. during in-situ material deposition), additional mathematics is required. The following equations are derived by algebraically inverting the previous equations, and transforming the effective PSI and DELTA measured in the presence of lenses into true PSI and DELTA values of a sample system:

C2P=cos 2φP; S2P=sin 2φP; C2A=cos 2φA; S2A=sin 2φA

Nwineff=cos(2·Ψwineff)

Cwineff=sin(2·wineff)·cos(Δwineff)

Swineff=sin(2·wineff)·sin(Δwineff)

$$s1 = \frac{(C2P - Nwineff)}{1 - Nwineff \cdot C2P}$$

$$s2 = \frac{Cwineff \cdot S2P}{1 - Nwineff \cdot C2P}$$

$$s3 = \frac{-Swineff \cdot S2P}{1 - Nwineff \cdot C2P}$$

a=(cos δw2·s1+sin δw2·s3)  b=s2  c=−(sin δw2·s1−cos δw2·s3)

$$Ntrue = \frac{(a - \cos\delta w1 \cdot C2P)}{(a \cdot \cos\delta w1 \cdot C2P - 1)}$$

$$Ctrue = \frac{(c \cdot \sin\delta w1 \cdot C2P + S2P \cdot b) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$$

$$Strue = \frac{(b \cdot \sin\delta w1 \cdot C2P - S2P \cdot c) \cdot (\cos\delta w1^2 \cdot C2P^2 - 1)}{(\sin\delta w1^2 \cdot C2P^2 + S2P^2) \cdot (a \cdot \cos\delta w1 \cdot C2P - 1)}$$

Ψtrue=a cos(Ntrue)·0.5

Δtrue=a tan 2 (Strue, Ctrue)−DeltaOffset

Two roots are calculated by the choosing the sign of the "Swineff" term. Note that when the lens correction terms (δw1) and (δw2) are zero (0.0), the two roots reduce to (+/−Δ), the expected ambiguity for a Rotating Analyzer ellipsometer system.

Continuing, where a Rotating Compensator ellipsometer system is present, use of the same Mueller matrix formalism as for the Rotating Analyzer ellipsometer system, the Fourier coefficients for the Rotating Compensator ellipsometer system can also be derived. The same orthogonalization approach to deriving second order lens effects was utilized, (ie. setting the fast axis of lens bi-refringence to forty-five (45) degrees), to determine the out-of-plane lens bi-refringence, with the in-plane component being added directly to sample system DELTA. (Note, in the following equations the (δ) is the retardance of the compensator system.

$$DC = \left[\frac{1}{2} \cdot (1 + \cos\delta) \cdot \begin{pmatrix} -C2P \cdot \cos\delta w1 \cdot N + C2P \cdot \cos\delta w1 \cdot C2A \cdot \cos\delta w2 + \\ C2P \cdot \sin\delta w1 \cdot S2A \cdot S - C2P \cdot \sin\delta w1 \cdot C2A \cdot \sin\delta w2 \cdot C + \\ S2P \cdot S2A \cdot C + S2P \cdot C2A \cdot \sin\delta w2 \cdot S \end{pmatrix}\right] +$$

$$1 - C2A \cdot \cos\delta w2 \cdot N$$

$$\alpha 2 = -\begin{pmatrix} \sin\delta w1 \cdot N - \sin\delta w1 \cdot C2A \cdot \cos\delta w2 + \\ \cos\delta w1 \cdot S2A \cdot S - \cos\delta w1 \cdot C2A \cdot \sin\delta w2 \cdot C \end{pmatrix} \cdot \sin\delta \cdot S2P$$

$$\beta 2 = -\begin{pmatrix} -\sin\delta w1 \cdot N - \sin\delta w1 \cdot C2A \cdot \cos\delta w2 + \\ -\cos\delta w1 \cdot S2A \cdot S + \cos\delta w1 \cdot C2A \cdot \sin\delta w2 \cdot C \end{pmatrix} \cdot \sin\delta \cdot C2P$$

$$\alpha 4 =$$
$$\frac{1}{2} \cdot (1 - \cos\delta) \cdot \begin{pmatrix} -C2P \cdot \cos\delta w1 \cdot N + C2P \cdot \cos\delta w1 \cdot C2A \cdot \cos\delta w2 + \\ C2P \cdot \sin\delta w1 \cdot S2A \cdot S - C2P \cdot \sin\delta w1 \cdot C2A \cdot \sin\delta w2 \cdot C + \\ -S2P \cdot S2A \cdot C - S2P \cdot C2A \cdot \sin\delta w2 \cdot S \end{pmatrix}$$

$$\beta 4 = \frac{1}{2} \cdot (1 - \cos\delta) \cdot \begin{pmatrix} C2P \cdot S2A \cdot C + C2P \cdot C2A \cdot \sin\delta w2 \cdot S - S2P \cdot \cos\delta w1 \cdot N + \\ +S2P \cdot \cos\delta w1 \cdot C2A \cdot \cos\delta w2 + \\ S2P \cdot \sin\delta w1 \cdot S2A \cdot S - S2P \cdot \sin\delta w1 \cdot C2A \cdot \sin\delta w2 \cdot C \end{pmatrix}$$

As in the Rotating Analyzer or Rotating Polarizer ellipsometer system case, a global regression calibration can be used to find the Rotating Compensator ellipsometer system calibration parameter values, in addition to out-of-plane lens parameterized equation values. And as described infra herein for the Rotating Analyzer ellipsometer system, a standard model fit with a parameterizable sample in place can be carried out to determine values for parameters in-plane.

It is noted that an advantage of the Rotating Compensator ellipsometer system is that it can correctly measure ellipsometric DELTAS over the full range of zero (0.0) to three-hundred-sixty (360) degrees. This implies that the true PSI and DELTA parameters can be directly inverted at data acquisition time from the measured Fourier Coefficients (ie. ALPHA and BETA), assuming that parameters in parametric lens correction equations for retardance have been previously determined. The inversion equations are:

$$\Psi = \frac{1}{2} \cdot \text{atan} \left[ \frac{\sqrt{\left[ \frac{(\cos\delta w1 \cdot (1 - \cos\delta) \cdot (-S2P \cdot a2 + C2P \cdot b2)) +}{2 \cdot \sin\delta \cdot \sin\delta w1 \cdot (a4 \cdot C2P + b4 \cdot S2P)}\right]^2 + 4 \cdot (-a4 \cdot S2P + C2P \cdot b4)^2}}{\left[ (2 \cdot \cos\delta w1 \cdot (a4 \cdot C2P + b4 \cdot S2P)) + \frac{(1 - \cos\delta)}{\sin\delta} \cdot \sin\delta w1 \cdot (S2P \cdot a2 - C2P \cdot b2) \right]} \right]$$

$$\Delta = \left[ \text{atan2} \left[ \begin{array}{l} ((1 - \cos\delta) \cdot \cos\delta w1 \cdot (b2 \cdot C2P \cdot a2 \cdot S2P)) + \\ 2 \cdot \sin\delta \cdot \sin\delta w1 \cdot (a4 \cdot C2P + b4 \cdot S2P) \end{array} \right], \right.$$
$$\left. 2 \cdot \sin\delta \cdot (b4 \cdot C2P - a4 \cdot S2P) \right] + \text{Delta\_Offset}$$

It Is noted that, with a bit of algebra, all the equations for the Rotating Compensator ellipsometer system can be reduced to first order expressions as given in the Kleim et al. reference cited in the Background Section.

In summary, the present invention demonstrates that a methodology for acquiring ellipsometric data through lenses has been developed and tested. The key insight enabling said accomplishment is that lens bi-refringence can be split into "out-of-plane" and "in-plane" components, where the "plane" referred to is the plane of incidence of an electromagnetic beam of radiation with respect to a sample system. Splitting the electromagnetic beam into said orthogonal components allows derivation of second order lens corrections which were tractable while allowing an ellipsometer system calibration procedure to determine values of parameters. Again, said ellipsometer system calibration procedure allows parameter values in "out-of-plane" component retardation representing equations to be directly evaluated, with the "in-plane" component being an additive factor to a sample system DELTA. A separate step, utilizing a sample system for which retardation can be modeled by a parameterized equation, allows evaluation of the parameters in parametric equations for the "in-plane" components of lenses separately. Work reported in the literature by other researchers regarding analogically similar window corrections provided equations which corrected only first order effects, and said equations have proven insufficient to correct for large, (eg. six (6) degrees), of retardation. (It is noted that prior work with respect to vacuum window corrections, orthogonal components were derived with respect to window fast axes, which is offset from the sample system plane of incidence). Where the window retardance becomes small, (eg. at longer wavelengths), parameter evaluation in equations for said orthogonal components becomes difficult, as it becomes difficult to determine fast axis orientation. This means that where fast axis orientation can not be identified, algorithm instability becomes a problem. Furthermore, the fast axis orientation of window retardance would also correlate with a sample system DELTA parameter unless a global regression fit using a parameterizable sample system is performed at calibration time.

The present invention methodology comprising two steps disclosed herein, fully and unambiguously determines lens correction terms in-situ.

After parameters in parameterized equations for retardance are evaluated by the method of the present invention, ellipsometric data can be taken through lenses, (eg. converging input and diverging output), and said data can be quickly and accurately analyzed by applying the correction factors in a mathematical model for a sample system, (in the case where a Rotating Analyzer ellipsometer system was used to acquire data), or the lens effects can be simply quantitatively subtracted away to yield "true" ellipsometric PSI and DELTA values, (in the case where a Rotating Compensator ellipsometer system was used to acquire data).

It should be appreciated that the methodology of the present invention is substantially the same as that disclosed in the Parent, Allowed but still Co-Pending application, Ser. No. 09/162,217 filed Sep. 29, 1998, with the difference being that the present invention provides comepnsation to converging input and diverging output lenses, (perhaps in combination with beam directing optics), rather than, or in addition to, to vacuum chamber windows, (which can be present as mathematically lumped-in with FIG. 1a1 (AC1) and (AC2) converging input and diverging output lenses). It is also noted that while achromatic multi-element converging input and diverging output lenses are preferred for application in the present invention, any lenses Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

What is claimed is:

1. An ellipsometer system comprising input and output lenses, said input and output lenses each being of multi-element construction, wherein, for each of said input and output lenses at least two elements thereof are made from different materials, such that in use the focal length for each wavelength in a range of wavelengths is essentially the same as that for every other wavelength, wherein said input and output lenses are characterized by a selection from the group consisting of:

both demonstrating birefringence;

one thereof demonstrating birefringence and the other not.

2. A polarimeter system comprising input and output lenses, said input and output lenses each being of multi-element construction, wherein, for each of said input and output lenses at least two elements thereof are made from different materials, such that in use the focal length for each wavelength in a range of wavelengths is essentially the same as that for every other wavelength, wherein said input and output lenses are characterized by a selection from the group consisting of:

both demonstrating birefringence;

one thereof demonstrating birefringence and the other not.

\* \* \* \* \*